(12) United States Patent
Kear

(10) Patent No.: US 8,052,694 B2
(45) Date of Patent: Nov. 8, 2011

(54) DEVICE FOR MANIPULATING MATERIAL IN A TISSUE

(75) Inventor: Jason Kear, Bloomington, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1184 days.

(21) Appl. No.: 10/423,599

(22) Filed: Apr. 25, 2003

(65) Prior Publication Data
US 2004/0186485 A1 Sep. 23, 2004

Related U.S. Application Data

(60) Provisional application No. 60/455,758, filed on Mar. 19, 2003.

(51) Int. Cl.
*A61B 17/22* (2006.01)
(52) U.S. Cl. ........... 606/127; 604/264
(58) Field of Classification Search ............ 606/2.5, 606/113, 127, 200, 110, 114, 128, 159; 604/264, 604/265
See application file for complete search history.

(56) References Cited

U.S. PATENT DOCUMENTS

| | | | |
|---|---|---|---|
| 4,425,908 A | 1/1984 | Simon | 128/1 R |
| 5,217,465 A | 6/1993 | Steppe | |
| 5,441,499 A | 8/1995 | Fritzsch | |
| 5,484,384 A * | 1/1996 | Fearnot | 600/3 |
| 5,501,654 A | 3/1996 | Failla et al. | |
| 5,509,923 A | 4/1996 | Middleman et al. | |
| 5,906,622 A | 5/1999 | Lippitt et al. | 606/127 |
| 6,068,645 A * | 5/2000 | Tu | 606/200 |
| 6,099,534 A * | 8/2000 | Bates et al. | 606/127 |
| 6,224,612 B1 | 5/2001 | Bates et al. | 606/114 |
| 6,231,544 B1 * | 5/2001 | Tsugita et al. | 604/104 |
| 6,325,807 B1 * | 12/2001 | Que | 606/127 |
| 6,350,266 B1 * | 2/2002 | White et al. | 606/114 |
| 6,371,971 B1 * | 4/2002 | Tsugita et al. | 606/200 |
| 6,398,791 B1 | 6/2002 | Que et al. | 606/127 |
| 6,500,182 B2 | 12/2002 | Foster | 606/127 |
| 6,695,834 B2 * | 2/2004 | Gellman et al. | 606/2.5 |
| 2001/0041899 A1 | 11/2001 | Foster | |
| 2002/0068954 A1 | 6/2002 | Foster | 606/200 |
| 2002/0133171 A1 | 9/2002 | Bourne et al. | |

FOREIGN PATENT DOCUMENTS

| | | |
|---|---|---|
| DE | 36 41 935 | 6/1987 |
| DE | 44 42 439 | 6/1996 |
| EP | 0 473 790 | 3/1992 |

OTHER PUBLICATIONS

U.S. Appl. No. 60/395,280, filed Jul. 2002, Foster et al.*
PCT International Search Report for International Application No. PCT/US2004/006079, dated Jul. 16, 2004.

* cited by examiner

*Primary Examiner* — Victor Nguyen
(74) *Attorney, Agent, or Firm* — Finnegan Henderson Farabow Garrett & Dunner, L.L.P.

(57) ABSTRACT

A medical device for manipulation of material in a tissue includes a sheath, an object engaging unit, and a flexible coupler. The object engaging unit has an operative end and a base. The flexible coupler includes a longitudinal axis and a distal portion; the distal portion is associated with the base of the object engaging unit and is bendable in an arc to various ranges. The flexible coupler confers lateral movement on the object engaging unit thereby permitting manipulation and/or retrieval of material lodged or disposed in heretofore often inaccessible tissue regions. The sheath has a longitudinal axis and a lumen. The object engaging unit is in a collapsed position when it is within the sheath lumen and an expanded position when it is extended beyond the sheath.

48 Claims, 4 Drawing Sheets

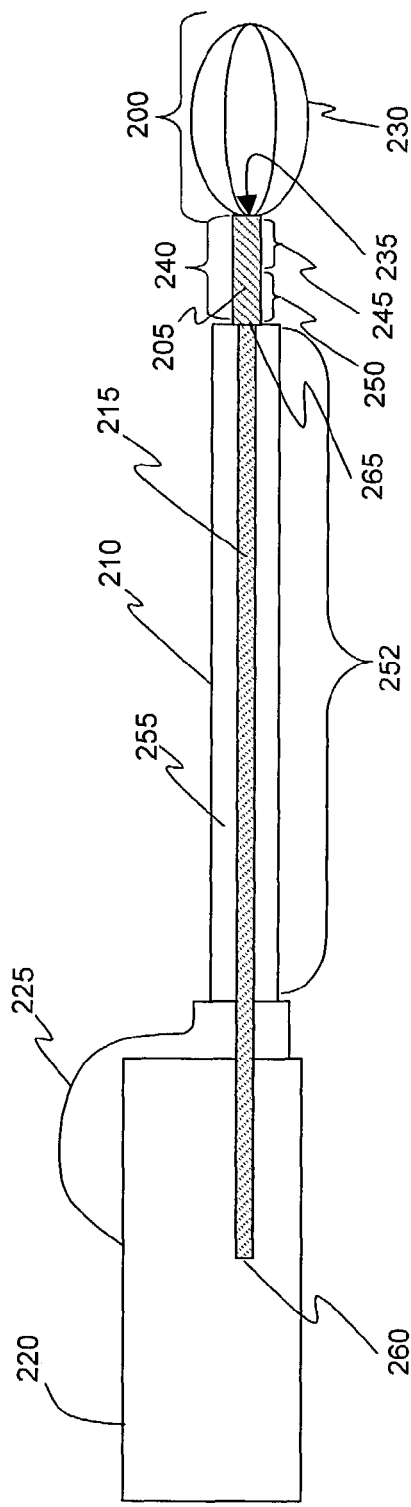
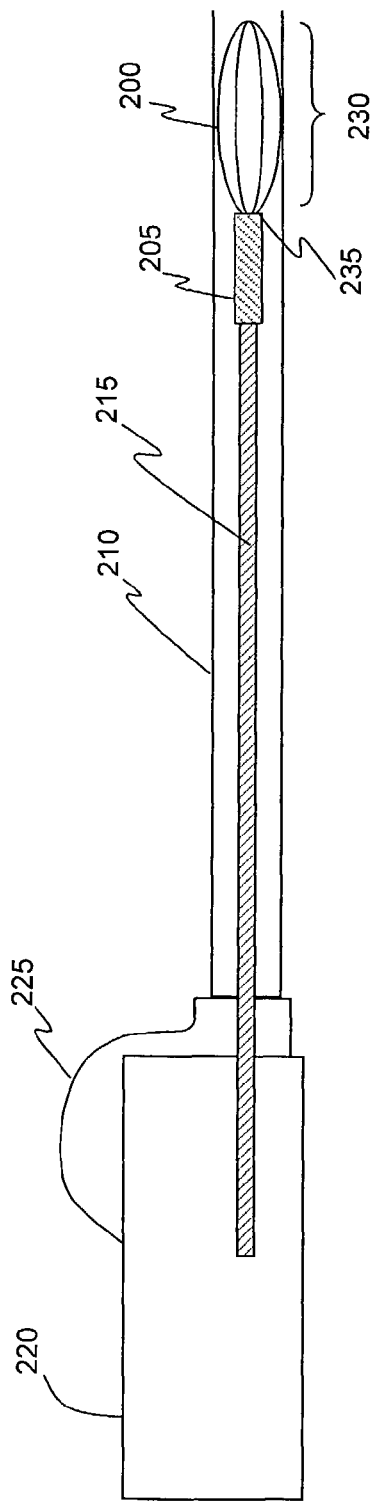
FIG. 2A
FIG. 2B

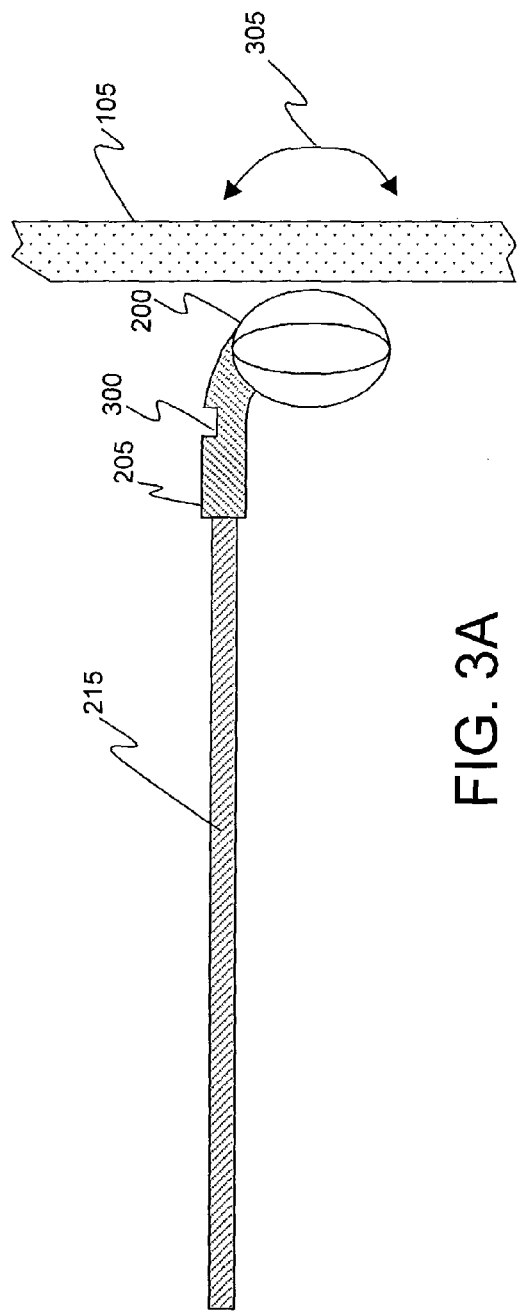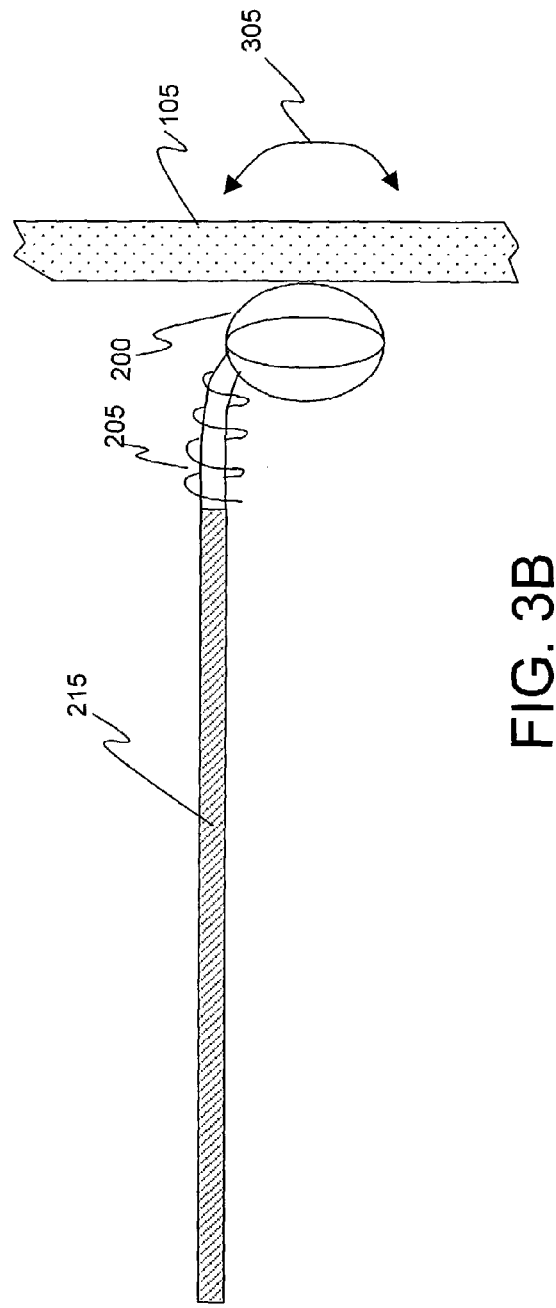

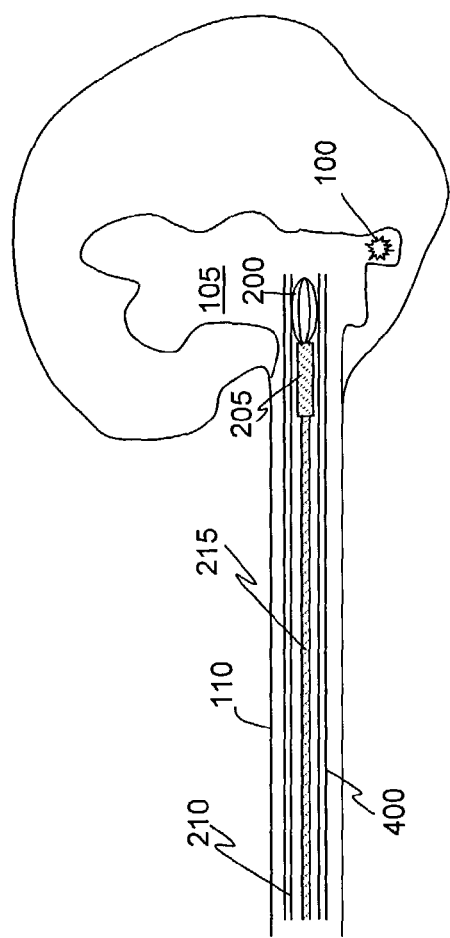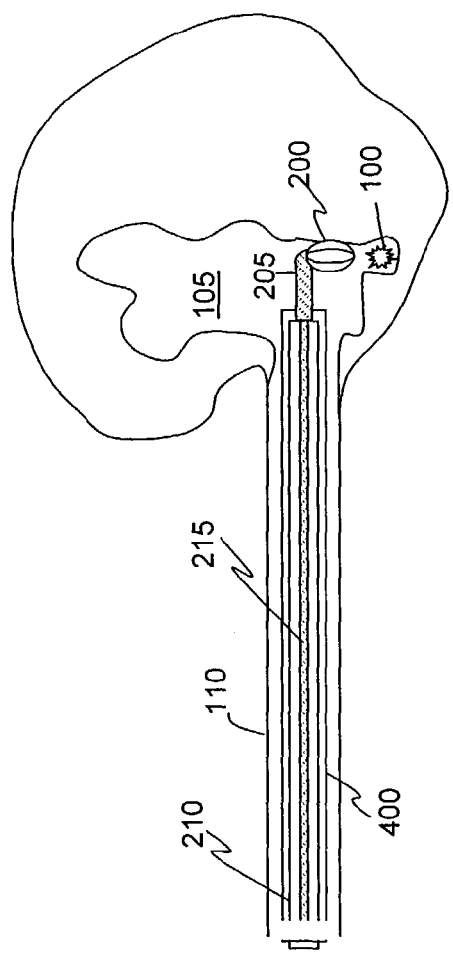

DEVICE FOR MANIPULATING MATERIAL IN A TISSUE

RELATED APPLICATION DATA

This application claims the benefit of U.S. provisional patent application 60/455,758 filed on Mar. 19, 2003, entitled FLEXIBLE BASKET CANNULA, the entire contents of which is herein incorporated by reference.

TECHNICAL FIELD

This invention generally relates to devices for manipulating material in a tissue or body opening. More particularly, the invention relates to a medical device, including an object engaging unit, such as a retrieval device, and a flexible coupler, for capturing or accessing material disposed or lodged in tissue, especially "pockets" or other areas that are difficult to access, for example.

BACKGROUND INFORMATION

Medical devices can be used to manipulate material lodged or disposed in a body opening, cavity, tract, or tissue directly or through an endoscope. One such routinely used medical device has an object engaging unit such as a basket, and a coupler such as a cannula that is traditionally made from an inflexible material such as stainless steel. The coupler is disposed at the base of the object engaging unit and couples the object engaging unit to other components in the medical device. Typically, the object engaging unit and the coupler are moveable relative to an overlaying sheath, from a collapsed position within the sheath to an expanded position in which the object engaging unit and the coupler extend past the distal end of the sheath. In the expanded position, the object engaging unit can be positioned and is operable at least to manipulate material, such as kidney stones, in a tissue.

When the material is lodged or disposed in narrow and/or convoluted regions of tissue, it would be advantageous for the object engaging unit's lateral movement to be unlimited in order to enhance the chance of the material being engaged, captured or retrieved successfully. However, due to the inflexible coupler that is typically joined to an object engaging unit, the lateral flexing motion of the object engaging unit found in standard medical devices is limited. Because the standard object engaging unit cannot easily make discrete lateral movements which are independent in part from the whole coupler, any lateral movement of the object engaging unit per se requires generous operating space within a tissue or body opening. Such a limitation on the movement of an object engaging unit is detrimental to the object engaging unit's ability to operate successfully in narrow and/or convoluted configurations in a tissue or body opening.

SUMMARY OF THE INVENTION

The discovery described herein confers optimal lateral movement on an object engaging unit thereby permitting manipulation and/or retrieval of material lodged or disposed in heretofore difficult to access tissue regions. By coupling an object engaging unit, such as a basket, to a medical device through a flexible coupler as described herein, the object engaging unit can make discrete lateral movements, not just longitudinal movements. Rather than just advancing incrementally in a straight-forward movement, the medical device of the present invention can discretely flex from side-to-side and assume a path that conforms to the contours of the tissue. Using the invention described herein, clinicians can now access remote tissue regions more reliably while also reducing the likelihood of tissue damage caused by the standard medical device having an inflexible coupler.

In a general aspect, the invention relates to an assembly for manipulation of material in a tissue. The assembly includes an object engaging unit and a flexible coupler. The object engaging unit has an operative end and a base, and is adapted to flex laterally. The flexible coupler is adjacent to and is in direct communication with the base of the object engaging unit. At least a portion of the flexible coupler laterally flexes with the object engaging unit.

As contemplated herein, the invention further relates to a medical device for manipulation of material in a tissue. The medical device includes a sheath, an object engaging unit, and a flexible coupler. The sheath has a longitudinal axis and a lumen. The object engaging unit has an operative end and a base. The object engaging unit is in a collapsed position when it is within the sheath lumen and an expanded position when it is extended beyond the sheath. The flexible coupler includes a longitudinal axis and a distal portion. The distal portion is associated with the base of the object engaging unit and is bendable in an arc in the range of between about 0 degrees and about 360 degrees relative to the long axis of the sheath.

In another embodiment of the device, the flexible coupler is bendable in an arc in the range of between about 0 degrees and about 180 degrees relative to the long axis of the sheath. In yet another embodiment of the device, the flexible coupler is bendable in an arc in the range of between about 0 degrees and about 135 degrees relative to the long axis of the sheath. In still another embodiment, the flexible coupler is bendable in an arc in the range of between about 0 degrees and about 90 degrees relative to the long axis of the sheath. In certain other embodiments of the device, the flexible coupler is bendable in an arc in the range of between about 0 degrees and about 45 degrees relative to the long axis of the sheath.

Also in accordance with the invention, in one embodiment, the flexible coupler includes a flexible cannula, which can be injection molded. In another embodiment of the medical device according to this aspect of the invention, the flexible coupler can also include a proximal portion joined to a handle. In a related embodiment, the medical device can further include an elongated member that has a proximal end joined to a handle and a distal end associated with the flexible coupler. The medical device of the present invention can further include an actuator that is coupled to the proximal end of the elongated member.

Also in accordance with this aspect of the invention, in one embodiment, the flexible coupler is made of a bio-compatible material, such as, plastic, metal and heat-shrink polymer. The plastic bio-compatible material can be polyurethane, ethylene vinyl acetate, polyethylene, polyether block amides, nylon, and polytetrafluoethylene (PTFE). The metal material can be a metal coil fabricated from a flexible material, and can include an elastic or super-elastic material, such as stainless steel, nitinol and titanium, for example. The heat shrink polymer material can include, but is not limited to, polytetrafluoethylene (PTFE), fluorinated ethylene propylene (FEP), ethylene vinyl acetate (EVA), polyester, and other polyolefins.

In one embodiment, the object engaging unit in the medical device has a plurality of legs (such as wire filaments) that converge at the base of the object engaging unit and are securely associated with the flexible coupler. In a related embodiment, the flexible coupler includes an adhesive-receiving aperture.

In another aspect, the invention provides a method of manipulating material in a tissue by providing a medical device that has a sheath, an object engaging unit and a flexible coupler for manipulation of material in a tissue. The sheath has a longitudinal axis and a lumen. The object engaging unit has an operative end and a base. The object engaging unit is in a collapsed position when it is within the sheath lumen and an expanded position when it is extended beyond the sheath. The flexible coupler includes a longitudinal axis and a distal portion. The distal portion is associated with the base of the object engaging unit and is bendable in an arc relative to the longitudinal axis of the sheath. The steps of the method can further include inserting the medical device into the tissue (either directly or through some other mechanism such as an endoscope channel). The steps of the method also include manipulating the material in the tissue by expanding the object engaging unit with the flexible coupler. Also in accordance with this aspect of the invention, in one embodiment, the medical device can be used within a fully deflectable ureteroscope.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 2A schematically depicts an exemplary embodiment of a medical device, including an object engaging unit and a flexible coupler according to the invention, in which the medical device is in an operative state.

FIG. 2B schematically depicts the medical device illustrated in FIG. 2A with the object engaging unit and the flexible coupler in a collapsed state.

FIG. 3A schematically depicts an exemplary embodiment of the object engaging unit and the flexible coupler shown in FIG. 2A, in which the object engaging unit and a portion of the coupler are flexed.

FIG. 3B schematically depicts another exemplary embodiment of the object engaging unit and the flexible coupler shown in FIG. 2A, in which the object engaging unit and a portion of the coupler are flexed.

FIG. 4A illustrates a step in a method of manipulating material in a tissue using a medical device including an embodiment of an object engaging unit and a flexible coupler according to the invention.

FIG. 4B illustrates another step in a method of manipulating material in a tissue using a medical device including an embodiment of an object engaging unit and a flexible coupler according to the invention.

DETAILED DESCRIPTION

Figure 1:
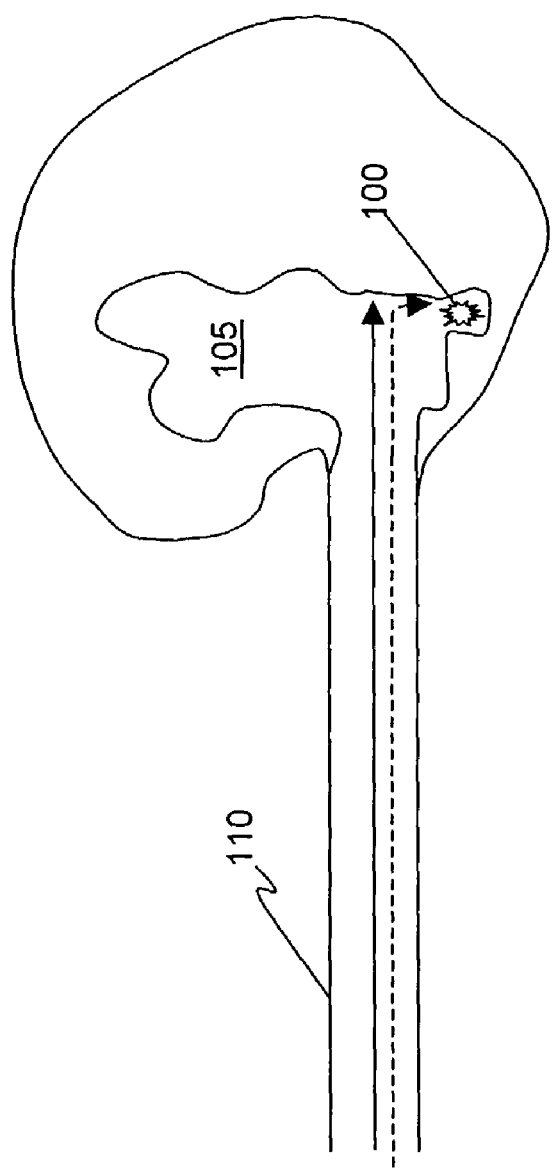
FIG. 1 schematically depicts a material lodged in a remote body cavity.

Among the problems encountered when using a medical device having an object engaging unit, such as a retrieval device, to manipulate a material at a remote location, are the turns and curves in the body tract or the tissue that must be negotiated in order to reach and actually manipulate the material at such a remote location. FIG. 1 illustrates, by way of example, a stone 100 lodged in the renal calyx 105 accessible via the ureter 110. In this example, the stone 100 is located in a pocket-type area that is closely surrounded by the walls or the linings of the renal calyx 105. Inevitably, the object engaging unit of the standard medical device entering the renal calyx often cannot move forward or further optimize its position relative to the deposited material without possibly damaging the tissue (solid arrow, FIG. 1).

In one embodiment, according to the present invention, at least a portion of a flexible coupler situated at or near the base of the object engaging unit is sufficiently flexible to allow the object engaging unit to move laterally. More specifically, the flexible coupler according to this invention is bendable in an arc to various degrees, so that when the object engaging unit reaches a tissue wall or similar obstruction that blocks the object engaging unit from moving forward, the object engaging unit can then move sufficiently laterally to navigate into and/or through narrow and convoluted spaces to reach the stone 100 (dotted arrow, FIG. 1). The object engaging unit's lateral flexibility allows it to move intimately along the surface of tissue, especially the walls or linings of a pocket-type area, to engage, manipulate and/or retrieve stones or other materials that may otherwise be unrecoverable using a standard object engaging unit that is associated with a conventional inflexible coupler, for example a solid-type stainless steel coupler.

Exemplary embodiments of the invention generally have at least the following features in common: an object engaging unit and a flexible coupler adjacent the object engaging unit. Referring to FIGS. 2A and 2B, one preferred embodiment of a medical device, according to the invention, includes an object engaging unit 200, a flexible coupler 205 disposed at a base 235 of the object engaging unit 200, a sheath 210, an elongated member 215, a handle 220, and an actuator 225. The handle 220, the sheath 210, the object engaging unit 200, and the flexible coupler 205 are not necessarily shown in their correct size or proportion to each other.

Referring again to FIGS. 2A and 2B, the object engaging unit 200 can include, for example, a grasping forceps-like assembly, a basket assembly as depicted, or any type of configuration useable for tissue and/or object engagement, manipulation, capture, and/or retrieval. Such assemblies can comprise various materials, configurations, and additional components. For example, the object engaging unit 200 can comprise a basket (FIG. 2A) with two or more legs that have various cross-sectional shapes (i.e., round, oval, square, wedge, etc.), various means of connection at the distal tip (i.e., integral, knotted, fused, alone or with fastener), and various materials (i.e., stainless steel, nitinol, etc.). A basket can assume various configurations (helical, egg-shaped, etc.), and may include additional components, such as coatings, webbing, etc. The object engaging unit 200 includes an operative end 230 and a base 235. The operative end 230 is the component that actually carries out the engagement, manipulation, capture and/or retrieval of material in a tissue. The operative end 230 can be, for example, a grasping forceps, a basket, a retractor, a probe, a needle, a scissors, or a surgical blade. The base 235 associates the operative end 230 with other components in the medical device assembly. The base 235 is not necessarily a discrete structure, although it can be in certain embodiments. In certain other embodiments, the term "base" is used to define that portion of the object engaging unit 200, e.g., a basket, which is closest to the flexible coupler 205 and which is opposite the distal most portion of the operative end 230 of the object engaging unit 200.

The flexible coupler 205 is associated with the base 235 of the object engaging unit 200 in various ways. In one embodiment, the flexible coupler 205 and the base 235 of the object engaging unit 200 are two physically separate components joined in a functionally appropriate manner. In another embodiment, the flexible coupler 205 and the base 235 of the object engaging unit 200 are fabricated from the same material, so that they are formed as contiguous components. In yet another embodiment, the base 235 can operatively serve as the flexible coupler 205, and the flexible coupler 205 can also operatively serve as the base 235. In yet another embodiment, the flexible coupler 205 and the base 235 share one or more structural features. In all these embodiments, at least a portion of a distal portion 245 of the flexible coupler 205 is bendable laterally in an arc 305 to various degrees as illustrated in FIGS. 3A and 3B.

The flexible coupler 205 is made from or coated with any flexible bio-compatible material. Examples of bio-compatible material include, but are not limited to, plastic, metal, and heat-shrink polymer. In one embodiment, the heat-shrink polymer can include polytetrafluoethylene (PTFE), fluorinated ethylene propylene (FEP), ethylene vinyl acetate (EVA) polyester, and other polyolefins.

In one preferred embodiment, the flexible coupler 205 occupies longitudinal axis 240, which has a distal portion 245 (i.e., the portion nearest the operative end 230), and a proximal portion 250 (i.e., the portion furthest away from the operative end 230). The distal portion 245 and the proximal portion 250 shown in FIG. 2A represent one instance where the lengths of the distal portion 245 and the proximal portion 250 are substantially equivalent. In other instances, the length of the distal portion 245 can be less or more than the proximal portion 250 of the flexible coupler 205. In certain embodiments, the object engaging unit 200, e.g., a basket, can flex laterally together with only the distal portion 245 of the flexible coupler 205, while under certain other embodiments, the object engaging unit 200 can flex laterally together with the distal portion 245 and at least a portion of the proximal portion 250 of the flexible coupler 205.

In some embodiments, the longitudinal axis 240 of the flexible coupler 205 can be enwrapped by a casing that defines a lumen extending from the proximal end of the flexible coupler 205 to the distal end of the flexible coupler 205. In this embodiment, the actual length of the distal portion 245 that can move laterally can vary, depending on the flexibility of the material from which the flexible coupler 205 is fabricated and the degree of movement required by the object engaging unit 200 when in operation.

FIG. 3A illustrates one exemplary embodiment of the medical device having a polymer-based flexible coupler 205 disposed between a distal end 265 of the elongated member and the object engaging unit 200. In an alternate embodiment, the flexible coupler 205 comprises a flexible cannula that enwraps a portion of the base 235 and/or a portion of the elongated member 215. In such an embodiment, for example, the flexible cannula can be injection molded into the desired shape and placement.

In another embodiment, a metal-based flexible coupler 205 is a metal coil as illustrated in FIG. 3B. In this embodiment, the metal coil is disposed between the distal end 265 of the elongated member 215 and the object engaging unit 200, although in other embodiments it is contemplated that such a metal coil is contiguous with and a continuation of the elongated member 215. Examples of the metal material used in the metal coil include, but are not limited to, stainless steel, nitinol, and titanium.

The thickness of the flexible coupler 205 can be adjusted to further enhance the flexibility of the flexible coupler 205. For example, the inside diameter of the flexible coupler 205 may range from 0.010 inches to 0.100 inches and the outside diameter of the flexible coupler 205 may range from 0.014 inches to 0.125 inches.

As discussed previously, the flexible coupler 205 of the present invention confers to the object engaging unit 200 the ability to move laterally. The flexible coupler 205 can flex anywhere along its length sufficient to permit the object engaging unit 200 to move laterally; in some instances, the flexible coupler 205 will flex at its most distal portion 245, while, in other instances, the flexible coupler 205 will flex at its proximal portion 250. This is particularly useful when material is located in pocket-type areas or other hard-to-reach areas, especially when the forward movement of the object engaging unit 200 is blocked or hindered by a tissue barrier 105, such as a tissue wall or tissue lining, as illustrated in FIGS. 1, 3A, and 3B. Referring to FIG. 3A, the flexible coupler 205 confers to the object engaging unit 200 the ability to make discrete lateral movements, independently of the whole of the flexible coupler 205, because at least a portion of the flexible coupler 205, for example the distal portion 245, bends to various ranges which in turn accommodates discrete lateral movements by the object engaging unit 200. In one embodiment, the distal portion 245 of the flexible coupler 205 is bendable in an arc 305 in the range of between about 0 degrees and about 360 degrees relative to a longitudinal axis 252 of the sheath 210. In another embodiment, the distal portion 245 is bendable in the arc 305 in the range of between about 0 degrees and about 180 degrees relative to the longitudinal axis 252 of the sheath 210. In yet another embodiment, the distal portion 245 is bendable in the arc 305 in the range of between about 0 degrees and about 135 degrees relative to the longitudinal axis 252 of the sheath 210. In yet another embodiment, the distal portion 245 is bendable in the arc 305 in the range of between about 0 degrees and about 90 degrees relative to the longitudinal axis 252 of the sheath 210. In still another embodiment, the distal portion 245 is bendable in the arc 305 in the range of between about 0 degrees and about 45 degrees relative to the longitudinal axis 252 of the sheath 210. Similarly, as depicted in FIG. 3B, the metal coil coupler 205 confers to the object engaging unit 200 the ability to make discrete lateral movements by flexing at least a portion of the metal coil coupler, including the distal portion 245 in an arc 305 to various degrees as described above.

The present invention contemplates that the length of the flexible coupler can vary. All that is required is a length sufficient to confer lateral flexibility to the object engaging unit 200. In certain embodiments, the flexible coupler 205 is about 10 cm; in others, it can range from about 10 to 20 cm, preferably about 10 to 15 cm; or about 0.1 to 10 cm. In other embodiments, it can be coextensive with the elongated member. In yet others, it can be less than about 0.10 cm or greater than about 20 cm in length.

In one type of object engaging unit 200, the object engaging unit 200 is formed from wire filaments, for example, nitinol wires. On one end, the wire filaments are knotted together to form the operative end 230 and on the other end, the loose wire filaments form "legs," which converge at the base 235 and are typically captured by the flexible coupler 205. In one embodiment the flexible coupler 205 encases the legs of the operative end 230 received from the base 235. In another embodiment, the base 235 comprises legs of the object engaging unit 200 that extend substantially through the entire length of the flexible coupler 205 or beyond the proximal portion 250 of the flexible coupler 205. In yet another embodiment, the legs terminate at the proximal portion 250 of the flexible coupler 205. In this type of embodiment, the flexible coupler 205 according to the invention has an adhesive-receiving aperture 300 as illustrated in FIG. 3A. An amount of adhesive is applied to the inside of the flexible coupler 205 through the aperture 300 to prevent the legs of the operative end 230 from rotating or sliding with respect to one another and to maintain adequate spacing in the operative end 230. In one embodiment, adhesive, for example, LOCTITE® PRISM® 4013 Medical Device Adhesive by Henkel Loctite Corp. of Rocky Hill, Conn., is applied to the legs of the operative end 230 to hold the legs together before inserting them into the flexible coupler 205. In the same embodiment, another type of LOCTITE® adhesive, for example, LOCTITE® PRISM® 4014 Medical Device Adhesive by Henkel Loctite Corp. of Rocky Hill, Conn., is applied inside of the flexible coupler 205 to join the coupler 205 to the base 235 and the legs. It will be appreciated by the artisan of ordinary skill that any similar adhesive is suitable for the purposes described here. An adhesive-receiving aperture 300 can be used with any of the embodiments contemplated by the present invention. Furthermore, use of an adhesive is appropriate with any of the embodiments described herein, even those without an adhesive-receiving aperture 300.

In another embodiment, a metal coil flexible coupler 205 wraps around the legs of the operative end 230 in a spring-like manner to secure the legs in one place and maintain lateral flexibility of the operative end 230. In the above-described embodiments, the proximal portion 250 is further adapted for receiving the elongated member 215 so as to associate the elongated member 215 with the legs of the object engaging unit 200. In related but distinct embodiments, the proximal portion 250 of the flexible coupler 205 joins to or otherwise associates with the handle 220 via the elongated member 215. In an alternative embodiment, the flexible coupler 205 replaces the elongated member 215 and joins to or otherwise connects directly to the handle 220.

Referring again to FIG. 2A, in one embodiment of the medical device contemplated herein, the device comprises the sheath 210 having a longitudinal axis 252 and at least one lumen 255. The longitudinal axis 252 of the sheath 210 can be characterized as a wall that extends from the handle 220 to a distal end of the sheath 210. The longitudinal axis 240 defines the lumen 255 extending from a proximal end of the sheath to a distal end of the sheath 210. The lumen 255 in the distal end of the sheath is adapted for receiving the object engaging unit 200 and the flexible coupler 205. Furthermore, the elongated member 215, such as a cable, coil, shaft, guidewire, or mandril wire, extends within the sheath lumen 255 from the actuator 225 in the handle 220 to the flexible coupler 205. In certain embodiments, the length of the elongated member 215 can range between about 90 cm to 140 cm, but longer or shorter elongated members are contemplated herein. The elongated member 215 includes a proximal end 260 and a distal end 265. In certain embodiments, at least a portion of the distal end 265 of the elongated member 215 is inserted into the proximal portion 250 of the coupler 205. The proximal end 260 is coupled to the actuator 205 in the handle 220 to be controlled by the actuator 225.

Operation of the actuator 225 in the handle 220 by an operator causes the object engaging unit 200 and the flexible coupler 205 to move relative to the sheath 210 between a collapsed position within the distal end of the sheath 210, as illustrated in FIG. 2B, to an expanded position, where the object engaging unit 200 and the flexible coupler 205 extend beyond the sheath 210, as shown in FIG. 2A.

Alternatively, in another embodiment of the invention, the actuator 225 is joined to the sheath 210. Operation of the actuator 225 in this embodiment causes the sheath 210 to move relative to the object engaging unit 200, the flexible coupler 205, and the elongated member 215, such that the object engaging unit 200 and the flexible coupler 205 are moved between a collapsed position within the sheath lumen 255, illustrated in FIG. 2B, to an expanded position outside of the sheath 210 where the operative end 230 of the object engaging unit 200 expands to its operative position and the object engaging unit 200 and the flexible coupler 205 extend beyond the sheath 210 as illustrated in FIG. 2A.

With the object engaging unit 200 and the flexible coupler 205 withdrawn into and collapsed within the sheath lumen 255, as shown in FIG. 2B, the object engaging unit 200 is inserted into the body directly, or via an endoscope channel, e.g., a fully deflectable ureteroscope, to a remote internal site in the body where the target material 100 is located. In an instance where the object engaging unit 200 is used within a fully deflectable ureteroscope, the flexible coupler 205 confers to the object engaging unit 205 the ability to flex together with the sheath 210 and the channel of the ureteroscope to navigate into and/or through narrow and convoluted turns and curves in a body tract or tissue. The object engaging unit 200 is then moved relative to the sheath 210 and placed in the expanded position illustrated in FIG. 2A, such that the object engaging unit 200, in its operative position, is manipulated by the operator to engage the target material or tissue in the remote body site. The object engaging unit 200 can then be used to manipulate the material in the tissue. In certain instances following manipulation of the material by the object engaging unit 200, the object engaging unit 200 is at least partially withdrawn into the sheath lumen 255 of the distal end of the sheath 210 to avoid dislodgment of the material inside the body. By moving the object engaging unit 200 and the flexible coupler 205 axially relative to the sheath 210, or by moving the sheath 210 axially relative to the object engaging unit 200, the medical device is withdrawn from the body cavity.

The present invention also relates to a method for manipulating material in a tissue, such as a body tract or body canal, using a medical device including a sheath 210, an object engaging unit 200, and a flexible coupler 205. Referring to FIG. 4A, the medical device may be directly introduced into the patient or may be introduced via a channel of an endoscope 400 as illustrated in FIG. 4A. For example, the endoscope 400 is advanced by an operator via the lumen of the ureter 110 until the distal end of the endoscope 400 enters the patient's body site, such as the renal calyx 105, where the target material 100 is located. The medical device, including the object engaging unit 200 and the flexible coupler 205, collapsed within the sheath, is passed into the endoscope 400, until the distal end of the sheath 210 approaches the distal end of the endoscope 400. As shown in FIG. 4B, the object engaging unit 200 and the flexible coupler 205 are extended beyond the sheath 210 to manipulate the material 100 in a tissue within the remote body site 110. The expanded object engaging unit 200 comprising the flexible coupler 205 can then make discrete lateral movements as at least the distal portion 245 of the flexible coupler 205 bends in an arc in various degrees, for example, in the range between about 0 degrees and 360 degrees relative to the longitudinal axis 252 of the sheath 210. Such lateral flexibility in the object engaging unit 200 enables the operator to reach the material 100 that is located in the pocket-type areas depicted in FIG. 4.

After the material or tissue 100 within the remote body site 105 is manipulated, the object engaging unit 200 is withdrawn partially or completely into the lumen 255 of the sheath 210 either by axial movement of the elongated member 215 or by movement of the longitudinal axis 252 of the sheath 210 over the stationary object engaging unit 200 and the flexible coupler 205.

The medical device including the sheath according to the invention can be directly inserted into a body cavity without an endoscope (not shown). The steps are similar to those described above for use of the medical device in an endoscope. The object engaging unit 200 extends from the sheath lumen 255 in the manner described above for using the medical device in an endoscope. After the material in the body site is manipulated, the object engaging unit 200 is withdrawn partially or completely into the sheath lumen 255. The medical device is then withdrawn from the tissue.

Variations, modifications, and other instrumentations of what is described herein will occur to those of ordinary skill in the art without departing from the spirit and scope of the invention as claimed. Accordingly, the invention is to be defined not by the preceding illustrative description but instead by the spirit and scope of the following claims.

What is claimed is:

1. A medical device for manipulation of material in a tissue, comprising:
   a sheath comprising a longitudinal axis and a sheath lumen;
   an object engaging unit having an operative end and a base, said object engaging unit having a collapsed position within the sheath lumen and an expanded position when extended distal to a distal end of the sheath;
   an elongated member; and
   a flexible coupler, disposed between the distal end of the elongated member and the object engaging unit, comprising a flexible cannula including a second lumen and enwrapping at least a portion of the base of the object engaging unit, wherein the at least a portion of the base is disposed within the second lumen, wherein the flexible cannula has a width greater than a width of the at least a portion of the base, the flexible coupler further comprising a longitudinal axis and a distal portion, the distal portion of the flexible coupler being associated with the base of the object engaging unit, and at least the distal portion of the flexible coupler being bendable in an arc relative to the longitudinal axis of the sheath, and wherein the flexible coupler and the base are the same piece of material and contiguous components of the medical device.

2. The medical device according to claim 1 wherein said flexible coupler further comprises a proximal portion joined to a handle.

3. The medical device according to claim 1 further comprising an actuator, wherein the actuator is coupled to the proximal end of the elongated member.

4. The medical device according to claim 1 further comprising an actuator, wherein the actuator is associated with the sheath.

5. The medical device according to claim 1 wherein at least the distal portion of the flexible coupler bends in an arc between about 0 degrees and about 360 degrees.

6. The medical device according to claim 1 wherein at least the distal portion of the flexible coupler bends in an arc between about 0 degrees and about 180 degrees.

7. The medical device according to claim 1 wherein at least the distal portion of the flexible coupler bends in an arc between about 0 degrees and about 135 degrees.

8. The medical device according to claim 1 wherein at least the distal portion of the flexible coupler bends in an arc between about 0 degrees and about 90 degrees.

9. The medical device according to claim 1 wherein at least the distal portion of the flexible coupler bends in an arc between about 0 degrees and about 45 degrees.

10. The medical device according to claim 1, wherein the flexible coupler is made of a bio-compatible material.

11. The medical device according to claim 10, wherein the bio-compatible material is selected from the group consisting of plastic, metal, and heat-shrink polymer.

12. The medical device according to claim 11, wherein the heat-shrink material is selected from the group consisting of polytetrafluoroethylene, flourinated ethylene propylene, ethylene vinyl acetate, polyester, and polyolefins.

13. The medical device according to claim 11, wherein the metal material is a metal coil.

14. The medical device according to claim 11, wherein the metal material is selected from the group consisting of stainless steel, nitinol, and titanium.

15. The medical device according to claim 1, wherein the object engaging unit comprises a plurality of wire filaments that converge at the base of said object engaging unit and are securely associated with the flexible coupler.

16. The medical device according to claim 1, wherein the flexible coupler further comprises an adhesive-receiving aperture.

17. The medical device of claim 16, wherein the adhesive-receiving aperture is formed on a side surface of the flexible coupler.

18. The medical device of claim 17, wherein the adhesive-receiving aperture extends entirely through the side surface of the flexible coupler.

19. The medical device according to claim 1, wherein the flexible cannula is injection molded.

20. The medical device according to claim 1, wherein the object engaging unit is disposed substantially completely distal to the flexible coupler.

21. The medical device according to claim 1, wherein the sheath maintains a substantially cylindrical configuration when the object engaging unit is in the expanded position.

22. The medical device according to claim 1, wherein the object engaging unit comprises a basket having at least two legs, the basket being one of substantially helical and substantially egg-shaped in the expanded position.

23. The medical device according to claim 22, wherein at least one of the legs has a cross-sectional shape that is one of substantially round, substantially ovular, substantially square, and substantially wedge-shaped.

24. The medical device of claim 1, wherein the flexible coupler is directly connected to the object engaging unit at the base.

25. The medical device of claim 1, wherein the base forms a closed proximal end of the object engaging unit.

26. The medical device of claim 1, wherein the operative end forms a closed distal end of the object engaging unit.

27. The medical device of claim 1, wherein the base of the object engaging unit extends through substantially an entire length of the flexible coupler.

28. The medical device of claim 1, wherein the flexible cannula enwraps at least a portion of the elongated member.

29. A method of manipulating material in a tissue, said method comprising the steps of:
   inserting a medical device for manipulation of material into a tissue, said device comprising:
      a sheath comprising a longitudinal axis and a sheath lumen;
      an object engaging unit having an operative end and a base, said object engaging unit having a collapsed position within the sheath lumen and an expanded position when extended distal to a distal end of the sheath;
      an elongated member; and
      a flexible coupler comprising a flexible cannula including a second lumen and enwrapping at least a portion of the base of the object engaging unit, wherein the at least a portion of the base is disposed within the second lumen, and wherein the flexible cannula has a width greater than a width of the at least a portion of the base, the flexible coupler being disposed between the distal end of the elongated member and the object engaging unit, comprising a longitudinal axis and a distal portion, the distal portion of the flexible coupler being associated with the base of the object engaging unit, and at least the distal portion of the flexible coupler being bendable in an arc relative to the longitudinal axis of the sheath, and wherein the flexible coupler and the base are the same piece of material and contiguous components of the medical device; and manipulating said material in the tissue with the object engaging unit.

30. The method of claim 29, wherein the object engaging unit is disposed substantially completely distal to the flexible coupler.

31. The method of claim 29, wherein the sheath maintains a substantially cylindrical configuration when the object engaging unit is in the expanded position.

32. The method of claim 29, wherein the flexible coupler is directly connected to the object engaging unit at the base.

33. The method of claim 29, wherein the base forms a closed proximal end of the object engaging unit.

34. The method of claim 29, wherein the base of the object engaging unit extends through substantially an entire length of the flexible coupler.

35. The method of claim 29, wherein the flexible cannula enwraps at least a portion of the elongated member.

36. An assembly for manipulation of material in a tissue, the assembly comprising:
   an object engaging unit having an operative end and a base, wherein said object engaging unit is adapted to flex laterally, said object engaging unit having an expanded position when extended distal to a distal end of a sheath of the assembly, the sheath including a sheath lumen;
   an elongated member; and
   a flexible coupler comprising a flexible cannula including a second lumen and enwrapping at least a portion of the base of the object engaging unit, wherein the at least a portion of the base is disposed within the second lumen, and wherein the flexible cannula has a width greater than a width of the at least a portion of the base, the flexible coupler being disposed between a distal end of the elongated member and the object engaging unit, and adjacent to and in direct communication with said base, wherein at least a portion of said flexible coupler laterally flexes with said object engaging unit, and wherein the flexible coupler and the base are the same piece of material and contiguous components of the medical device.

37. The assembly of claim 36, wherein the sheath maintains a substantially cylindrical configuration when the object engaging unit is in the expanded position.

38. The assembly of claim 36, wherein the base forms a closed proximal end of the object engaging unit.

39. The assembly of claim 36, wherein the base of the object engaging unit extends through substantially an entire length of the flexible coupler.

40. The assembly of claim 36, wherein the flexible cannula enwraps at least a portion of the elongated member.

41. A medical device for manipulation of material in a tissue, comprising:
   a sheath comprising a longitudinal axis and a sheath lumen;
   an object engaging unit having an operative end and a base, said object engaging unit having a collapsed position within the sheath lumen and an expanded position when extended distal to a distal end of the sheath; and
   a flexible coupler comprising a second lumen, a longitudinal axis, and a distal portion, the distal portion of the flexible coupler being associated with the base of the object engaging unit, wherein at least a portion of the base is disposed within the second lumen, wherein the flexible coupler has a width greater than a width of the at least a portion of the base, at least the distal portion of the flexible coupler being bendable in an arc relative to the longitudinal axis of the sheath, and wherein the flexible coupler and the base are formed from the same piece of material as contiguous components of the medical device.

42. The medical device of claim 41, wherein the distal end of an elongated member associates with the proximal end of the flexible coupler.

43. A medical device for manipulation of material in a tissue, comprising:
   a sheath comprising a longitudinal axis and a sheath lumen;
   an object engaging unit having an operative end and a base, said object engaging unit having a collapsed position within the sheath lumen and an expanded position when extended distal to a distal end of the sheath;
   an elongated member; and
   a flexible coupler, disposed between the distal end of the elongated member and the object engaging unit, comprising a second lumen, a longitudinal axis, and a distal portion, the distal portion of the flexible coupler being associated with the base of the object engaging unit, wherein at least a portion of the base is disposed within the second lumen, wherein the flexible coupler has a width greater than a width of the at least a portion of the base, at least the distal portion of the flexible coupler being bendable in an arc relative to the longitudinal axis of the sheath, and wherein the flexible coupler further comprises an adhesive-receiving aperture.

44. The medical device of claim 43, wherein the adhesive-receiving aperture is formed on a side surface of the flexible coupler.

45. The medical device of claim 44, wherein the adhesive-receiving aperture extends entirely through the side surface of the flexible coupler.

46. A medical device for manipulation of material in a tissue, comprising:
   a sheath comprising a longitudinal axis and a sheath lumen;
   an object engaging unit having an operative end and a base, said object engaging unit having a collapsed position within the sheath lumen and an expanded position when extended distal to a distal end of the sheath;
   an elongated member; and
   a flexible coupler, disposed between the distal end of the elongated member and the object engaging unit, comprising a flexible cannula including a second lumen, a longitudinal axis, and a distal portion, the distal portion of the flexible coupler being associated with the base of the object engaging unit, wherein at least a portion of the base is disposed within the second lumen, wherein the flexible cannula has a width greater than a width of the at least a portion of the base, at least the distal portion of the flexible coupler being bendable in an arc relative to the longitudinal axis of the sheath, wherein the base of the object engaging unit extends through substantially an entire length of the flexible coupler, and wherein the flexible coupler and the base are the same piece of material and contiguous components of the medical device.

47. The medical device of claim 46, wherein the flexible cannula enwraps the at least a portion of the base of the object engaging unit and at least a portion of the elongated member.

48. The medical device according to claim 46, wherein the flexible coupler further comprises an adhesive-receiving aperture.

* * * * *